United States Patent
Schmidt et al.

(10) Patent No.: US 10,535,420 B2
(45) Date of Patent: Jan. 14, 2020

(54) SYSTEMS AND METHODS FOR PROBE DESIGN TO DETECT THE PRESENCE OF SIMPLE AND COMPLEX INDELS

(71) Applicant: Affymetrix, Inc., Santa Clara, CA (US)

(72) Inventors: Jeanette Pruzan Schmidt, Santa Clara, CA (US); Christopher Davies, Santa Clara, CA (US); Brant Wong, Santa Clara, CA (US)

(73) Assignee: Affymetrix, Inc., Carlsbad, CA (US)

( * ) Notice: Subject to any disclaimer, the term of this patent is extended or adjusted under 35 U.S.C. 154(b) by 738 days.

(21) Appl. No.: 13/844,567

(22) Filed: Mar. 15, 2013

(65) Prior Publication Data

US 2014/0274728 A1    Sep. 18, 2014

(51) Int. Cl.
*G16B 25/00* (2019.01)
(52) U.S. Cl.
CPC .................................. *G16B 25/00* (2019.02)
(58) Field of Classification Search
None
See application file for complete search history.

(56) References Cited

U.S. PATENT DOCUMENTS

| | | | |
|---|---|---|---|
| 5,412,087 A | 5/1995 | McGall et al. |
| 5,547,839 A | 8/1996 | Dower et al. |
| 5,733,729 A | 3/1998 | Lipshutz et al. |
| 5,762,876 A | 6/1998 | Lincoln et al. |
| 5,834,758 A | 11/1998 | Trulson et al. |
| 5,874,219 A | 2/1999 | Rava et al. |
| 5,889,165 A | 3/1999 | Fodor et al. |
| 5,959,098 A | 9/1999 | Goldberg et al. |
| 6,066,454 A | 5/2000 | Lipshutz et al. |
| 6,141,096 A | 10/2000 | Stern et al. |
| 6,147,205 A | 11/2000 | McGall et al. |
| 6,185,030 B1 | 2/2001 | Overbeck et al. |
| 6,185,561 B1 | 2/2001 | Balaban et al. |
| 6,188,783 B1 | 2/2001 | Balaban et al. |
| 6,201,639 B1 | 3/2001 | Overbeck et al. |
| 6,218,803 B1 | 4/2001 | Montagu et al. |
| 6,223,127 B1 | 4/2001 | Berno et al. |
| 6,225,625 B1 | 5/2001 | Pirrung et al. |
| 6,229,911 B1 | 5/2001 | Balaban |
| 6,262,216 B1 | 7/2001 | McGall |
| 6,308,170 B1 | 10/2001 | Balaban et al. |
| 6,310,189 B1 | 10/2001 | Fodor et al. |
| 6,386,749 B1 | 5/2002 | Watts et al. |
| 6,391,623 B1 | 5/2002 | Besemer et al. |
| 6,420,108 B2 | 7/2002 | Mack et al. |
| 6,607,887 B2 | 8/2003 | Chee et al. |
| 6,872,529 B2 | 3/2005 | Su |
| 7,297,778 B2 | 11/2007 | Matsuzaki et al. |
| 7,300,788 B2 | 11/2007 | Matsuzaki et al. |
| 7,361,468 B2 | 4/2008 | Switzer |
| 7,689,022 B2 | 3/2010 | Weiner et al. |
| 7,881,875 B2 | 2/2011 | Webster et al. |
| 8,501,122 B2 | 8/2013 | Shirazi et al. |
| 2002/0150935 A1 | 10/2002 | Zhou et al. |
| 2003/0186279 A1 | 10/2003 | Kennedy et al. |
| 2003/0186280 A1 | 10/2003 | Kennedy et al. |
| 2004/0012676 A1 | 1/2004 | Weiner et al. |
| 2005/0019787 A1 | 1/2005 | Berno et al. |
| 2005/0023672 A1 | 2/2005 | Oostman et al. |
| 2005/0123971 A1 | 6/2005 | Di et al. |
| 2005/0260628 A1 | 11/2005 | Matsuzaki et al. |
| 2006/0218182 A1 | 9/2006 | Giffard et al. |
| 2007/0065816 A1 | 3/2007 | Dong et al. |
| 2008/0131894 A1 | 6/2008 | Fu et al. |
| 2011/0303027 A1 | 12/2011 | West |

FOREIGN PATENT DOCUMENTS

WO    WO 1999/047964 A1    3/1999

OTHER PUBLICATIONS

U.S. Appl. No. 60/493,495, Kaiser, et al., filed Aug. 8, 2003.
Albers, et al., (2011) "Dindel: Accurate indel calls from short-read data." *Genome Research*, 21(6): 961-973.
Bignell, et al. (2004) "High-Resolution Analysis of DNA Copy Number Using Oligonucleotide Microarrays." *Genome Research*, 14: 287-295.
Butcher, et al. (2004) "Genotyping Pooled DNA on Microarrays: A Systematic Genome Screen of Thousands of SNPs in Large Samples to Detect QTLs for Complex Traits." *Behavior Genetics*, 34(5): 549-555.
Cutler et al., (2001) "High throughput variation detection and genotyping using microarrays." *Genome Research*, 11: 1913-1925.
Daly, et al. (2001) "High-resolution haplotype structure in the human genome." *Nature Genetics*, 29: 229-232.
Di, et al., (2005) "Dynamic model based algorithms for screening and genotyping over 100K SNPs on oligonucleotide microarrays." *Bioinformatics*, 21(9): 1958-1963.
Gabriel, et al. (2002) "The Structure of Haplotype Blocks in the Human Genome." *Science*, 296: 2225-2229.
Gissen, et al. (2004) "Mutations in VPS33B, encoding a regulator of SNAREdependent membrane fusion, cause arthrogryposis—renal dysfunction—cholestasis (ARC) syndrome." *Nature Genetics*, 36(4): 400-404.
Herr, et al. (2005) "High-resolution analysis of chromosomal imbalances using the Affymetrix 10K SNP genotyping chip." *Genomics*, 85(3): 392-400.
Hoffmann, et al. (2011) "Design and coverage of high throughput genotyping arrays optimized for individuals of East Asian, African American, and Latino race/ethnicity using imputation and a novel hybrid SNP selection algorithm," *Genomics*, 98(6): 422-430.
Hoffmann, et al. (2011) "Next generation genome-wide association tool: design and coverage of a high-throughput European-optimized SNP array," *Genomics*, 98(2): 79-89.

(Continued)

*Primary Examiner* — Joseph Woitach
(74) *Attorney, Agent, or Firm* — Mauriel Kapouytian Woods LLP; Michael Mauriel

(57) ABSTRACT

Methods and systems for the determination of a collection of relevant single nucleotide polymorphisms (SNP) probe compatible insertion/deletion probes across a genome to determine probes that can detect a variety of insertions and deletions.

15 Claims, 2 Drawing Sheets

Specification includes a Sequence Listing.

(56) References Cited

OTHER PUBLICATIONS

Kanehisa, M. (1984) "Use of statistical criteria for screening potential homologies in nucleic acid sequences." *Nucleic Acids Research*, 12(1): 203-213.

Kendziorski, et al. (2005) "On the utility of pooling biological samples in microarray experiments." *PNAS*, 102: 4542-4547.

Kennedy, et al. (2003) "Large-scale genotyping of complex DNA." *Nature Biotechnology*, 21: 1233-1237.

Matsuzaki, et al., (2004) "Parallel Genotyping of Over 10,000 SNPs Using a One-Primer Assay on a High-Density Oligonucleotide Array." *Genome Research*, 14(3): 414-425.

Nielsen, et al. (1991) "Sequence-selective recognition of DNA by strand displacement with a thymine-substituted polyamide." *Science*, 254: 1497-1500.

Puffenberger, et al. (2004) "Mapping of sudden infant death with dysgenesis of the testes syndrome (SIDDT) by a SNP genome scan and identification of TSPYL loss of function." *PNAS*, 101(32): 11689-11694.

Rioux, et al. (2001) "Genetic variation in the 5q31 cytokine gene cluster confers susceptibility to Crohn disease." *Nature Genetics*, 29: 223-228.

Schaid, D. (2004) "Evaluating associations of haplotypes with traits." *Genetic Epidemiology*, 27(4): 348-364.

Schaid, D. (2005) "Power and Sample Size for Testing Associations of Haplotypes with Complex Traits." *Annals of Human Genetics*, 70(1): 116-130.

The 1000 Genomes Project Consortium (2012) "An integrated map of genetic variation from 1,092 human genomes." *Nature*, 491: 56-65.

The International SNP Map Working Group (2001) "A map of human genome sequence variation containing 1.42 million single nucleotide polymorphisms." *Nature*, 409: 928-933.

Young, R. and Davis, R. (1983) "Efficient isolation of genes by using antibody probes." *PNAS*, 80: 1194-1198.

SEQUENCE LISTING

```
<160> NUMBER OF SEQ ID NOS: 83

<210> SEQ ID NO 1
<211> LENGTH: 25
<212> TYPE: DNA
<213> ORGANISM: Artificial
<220> FEATURE:
<223> OTHER INFORMATION: exemplary indel
```

<400> SEQUENCE: 1
atgactgacg gttaactatc actcg                                         25

<210> SEQ ID NO 2
<211> LENGTH: 26
<212> TYPE: DNA
<213> ORGANISM: Artificial
<220> FEATURE:
<223> OTHER INFORMATION: exemplary indel

<400> SEQUENCE: 2
atgactgacg gttaaactat cactcg                                        26

<210> SEQ ID NO 3
<211> LENGTH: 25
<212> TYPE: DNA
<213> ORGANISM: Artificial
<220> FEATURE:
<223> OTHER INFORMATION: exemplary indel

<400> SEQUENCE: 3
tacgcagatc agccacgtac ttcgg                                         25

<210> SEQ ID NO 4
<211> LENGTH: 26
<212> TYPE: DNA
<213> ORGANISM: Artificial
<220> FEATURE:
<223> OTHER INFORMATION: exemplary indel

<400> SEQUENCE: 4
tacgcagatc agcgcacgta cttcgg                                        26

<210> SEQ ID NO 5
<211> LENGTH: 50
<212> TYPE: DNA
<213> ORGANISM: Artificial
<220> FEATURE:
<223> OTHER INFORMATION: exemplary indel

<400> SEQUENCE: 5
cccttggagc cagggtcgtt gagaccaggt aagccaggag gtccctaaat              50

<210> SEQ ID NO 6
<211> LENGTH: 53
<212> TYPE: DNA
<213> ORGANISM: Artificial
<220> FEATURE:
<223> OTHER INFORMATION: exemplary indel

<400> SEQUENCE: 6
cccttggagc cagggtcatc gttgagacca ggtaagccag gaggtcccta aat          53

<210> SEQ ID NO 7
<211> LENGTH: 54
<212> TYPE: DNA
<213> ORGANISM: Artificial
<220> FEATURE:
<223> OTHER INFORMATION: exemplary indel

<400> SEQUENCE: 7
cctgaggcct ggagcactga gtgaggggag ggtggctgtg gaggcgccgc tcta         54

<210> SEQ ID NO 8

```
<211> LENGTH: 56
<212> TYPE: DNA
<213> ORGANISM: Artificial
<220> FEATURE:
<223> OTHER INFORMATION: exemplary indel

<400> SEQUENCE: 8
cctgaggcct ggagcactga gtgagggcag agggtggctg tggaggcgcc gctcta         56

<210> SEQ ID NO 9
<211> LENGTH: 30
<212> TYPE: DNA
<213> ORGANISM: Artificial
<220> FEATURE:
<223> OTHER INFORMATION: oligonucleotide probe

<400> SEQUENCE: 9
cttggcacag tctagacatc tcaaactgct                                      30

<210> SEQ ID NO 10
<211> LENGTH: 66
<212> TYPE: DNA
<213> ORGANISM: Artificial
<220> FEATURE:
<223> OTHER INFORMATION: exemplary SNP

<400> SEQUENCE: 10
cttggcacag tctagacatc tcaaactgct atactatggg gcaagacccc tggaccaccc     60
aaccac                                                                66

<210> SEQ ID NO 11
<211> LENGTH: 66
<212> TYPE: DNA
<213> ORGANISM: Artificial
<220> FEATURE:
<223> OTHER INFORMATION: exemplary SNP

<400> SEQUENCE: 11
cttggcacag tctagacatc tcaaactgct ctactatggg gcaagacccc tggaccaccc     60
aaccac                                                                66

<210> SEQ ID NO 12
<211> LENGTH: 30
<212> TYPE: DNA
<213> ORGANISM: Artificial
<220> FEATURE:
<223> OTHER INFORMATION: oligonucleotide probe

<400> SEQUENCE: 12
tactatgggg caagacccct ggaccaccca                                      30

<210> SEQ ID NO 13
<211> LENGTH: 31
<212> TYPE: DNA
<213> ORGANISM: Artificial
<220> FEATURE:
<223> OTHER INFORMATION: oligonucleotide probe

<400> SEQUENCE: 13
ggcttctaga tggaatcagc agcggaaaac a                                    31

<210> SEQ ID NO 14
<211> LENGTH: 31
<212> TYPE: DNA
<213> ORGANISM: Artificial
```

```
<220> FEATURE:
<223> OTHER INFORMATION: oligonucleotide probe

<400> SEQUENCE: 14
ggcttctaga tggaatcagc agcggaaaag a                              31

<210> SEQ ID NO 15
<211> LENGTH: 65
<212> TYPE: DNA
<213> ORGANISM: Artificial
<220> FEATURE:
<223> OTHER INFORMATION: exemplary SNP

<400> SEQUENCE: 15
ggcttctaga tggaatcagc agcggaaaac aacaggaaga gatgaagaag caaaatcaac  60
aagac                                                             65

<210> SEQ ID NO 16
<211> LENGTH: 65
<212> TYPE: DNA
<213> ORGANISM: Artificial
<220> FEATURE:
<223> OTHER INFORMATION: exemplary SNP

<400> SEQUENCE: 16
ggcttctaga tggaatcagc agcggaaaag aacaggaaga gatgaagaag caaaatcaac  60
aagac                                                             65

<210> SEQ ID NO 17
<211> LENGTH: 31
<212> TYPE: DNA
<213> ORGANISM: Artificial
<220> FEATURE:
<223> OTHER INFORMATION: oligonucleotide probe

<400> SEQUENCE: 17
acaacaggaa gagatgaaga agcaaaatca a                              31

<210> SEQ ID NO 18
<211> LENGTH: 31
<212> TYPE: DNA
<213> ORGANISM: Artificial
<220> FEATURE:
<223> OTHER INFORMATION: oligonucleotide probe

<400> SEQUENCE: 18
agaacaggaa gagatgaaga agcaaaatca a                              31

<210> SEQ ID NO 19
<211> LENGTH: 31
<212> TYPE: DNA
<213> ORGANISM: Artificial
<220> FEATURE:
<223> OTHER INFORMATION: oligonucleotide probe

<400> SEQUENCE: 19
ttatatagaa aggctctaag taccttgggt a                              31

<210> SEQ ID NO 20
<211> LENGTH: 31
<212> TYPE: DNA
<213> ORGANISM: Artificial
<220> FEATURE:
<223> OTHER INFORMATION: oligonucleotide probe
```

<400> SEQUENCE: 20
ttatatagaa aggctctaag taccttgggt c                                31

<210> SEQ ID NO 21
<211> LENGTH: 60
<212> TYPE: DNA
<213> ORGANISM: Artificial
<220> FEATURE:
<223> OTHER INFORMATION: exemplary indel

<400> SEQUENCE: 21
ttatatagaa aggctctaag taccttgggt atgtaaaggt ggcctgaaga ctgccagaag    60

<210> SEQ ID NO 22
<211> LENGTH: 61
<212> TYPE: DNA
<213> ORGANISM: Artificial
<220> FEATURE:
<223> OTHER INFORMATION: exemplary indel

<400> SEQUENCE: 22
ttatatagaa aggctctaag taccttgggt catgtaaagg tggcctgaag actgccagaa    60
g                                                                  61

<210> SEQ ID NO 23
<211> LENGTH: 31
<212> TYPE: DNA
<213> ORGANISM: Artificial
<220> FEATURE:
<223> OTHER INFORMATION: oligonucleotide probe

<400> SEQUENCE: 23
tatgtaaagg tggcctgaag actgccagaa g                                 31

<210> SEQ ID NO 24
<211> LENGTH: 31
<212> TYPE: DNA
<213> ORGANISM: Artificial
<220> FEATURE:
<223> OTHER INFORMATION: oligonucleotide probe

<400> SEQUENCE: 24
catgtaaagg tggcctgaag actgccagaa g                                 31

<210> SEQ ID NO 25
<211> LENGTH: 30
<212> TYPE: DNA
<213> ORGANISM: Artificial
<220> FEATURE:
<223> OTHER INFORMATION: oligonucleotide probe

<400> SEQUENCE: 25
attctcacct tttcaccctt ggagccaggg                                   30

<210> SEQ ID NO 26
<211> LENGTH: 65
<212> TYPE: DNA
<213> ORGANISM: Artificial
<220> FEATURE:
<223> OTHER INFORMATION: exemplary indel

<400> SEQUENCE: 26
attctcacct tttcaccctt ggagccaggg cctttgagac caggtaagcc aggaggtccc    60
taaat                                                              65

```
<210> SEQ ID NO 27
<211> LENGTH: 68
<212> TYPE: DNA
<213> ORGANISM: Artificial
<220> FEATURE:
<223> OTHER INFORMATION: exemplary indel

<400> SEQUENCE: 27
attctcacct tttcaccctt ggagccaggg tcacctttga gaccaggtaa gccaggaggt      60
ccctaaat                                                                68

<210> SEQ ID NO 28
<211> LENGTH: 30
<212> TYPE: DNA
<213> ORGANISM: Artificial
<220> FEATURE:
<223> OTHER INFORMATION: oligonucleotide probe

<400> SEQUENCE: 28
ctctagaagc caaaatggga cacagtaaac                                        30

<210> SEQ ID NO 29
<211> LENGTH: 66
<212> TYPE: DNA
<213> ORGANISM: Artificial
<220> FEATURE:
<223> OTHER INFORMATION: exemplary indel

<400> SEQUENCE: 29
cctctagaag ccaaaatggg acacagtaaa cattcgaatt ttacttctga acgaaatgga      60
gaaact                                                                  66

<210> SEQ ID NO 30
<211> LENGTH: 68
<212> TYPE: DNA
<213> ORGANISM: Artificial
<220> FEATURE:
<223> OTHER INFORMATION: exemplary indel

<400> SEQUENCE: 30
cctctagaag ccaaaatggg acacagtaaa cagattcgaa ttttacttct gaacgaaatg      60
gagaaact                                                                68

<210> SEQ ID NO 31
<211> LENGTH: 30
<212> TYPE: DNA
<213> ORGANISM: Artificial
<220> FEATURE:
<223> OTHER INFORMATION: oligonucleotide probe

<400> SEQUENCE: 31
tctagaagcc aaaatgggac acagtaaaca                                        30

<210> SEQ ID NO 32
<211> LENGTH: 64
<212> TYPE: DNA
<213> ORGANISM: Artificial
<220> FEATURE:
<223> OTHER INFORMATION: exemplary indel

<400> SEQUENCE: 32
tctagaagcc aaaatgggac acagtaaaca ttcgaatttt acttctgaac gaaatggaga      60
``` aact 64

<210> SEQ ID NO 33
<211> LENGTH: 66
<212> TYPE: DNA
<213> ORGANISM: Artificial
<220> FEATURE:
<223> OTHER INFORMATION: exemplary indel

<400> SEQUENCE: 33
tctagaagcc aaaatgggac acagtaaaca gattcgaatt ttacttctga acgaaatgga 60
gaaact 66

<210> SEQ ID NO 34
<211> LENGTH: 30
<212> TYPE: DNA
<213> ORGANISM: Artificial
<220> FEATURE:
<223> OTHER INFORMATION: oligonucleotide probe

<400> SEQUENCE: 34
agccctgagg cctggagcac tgagtgaggg 30

<210> SEQ ID NO 35
<211> LENGTH: 65
<212> TYPE: DNA
<213> ORGANISM: Artificial
<220> FEATURE:
<223> OTHER INFORMATION: exemplary indel

<400> SEQUENCE: 35
agccctgagg cctggagcac tgagtgaggg gagggtggct gtggaggcgc cgctctatcc 60
acagg 65

<210> SEQ ID NO 36
<211> LENGTH: 67
<212> TYPE: DNA
<213> ORGANISM: Artificial
<220> FEATURE:
<223> OTHER INFORMATION: exemplary indel

<400> SEQUENCE: 36
agccctgagg cctggagcac tgagtgaggg cagagggtgg ctgtggaggc gccgctctat 60
ccacagg 67

<210> SEQ ID NO 37
<211> LENGTH: 31
<212> TYPE: DNA
<213> ORGANISM: Artificial
<220> FEATURE:
<223> OTHER INFORMATION: oligonucleotide probe

<400> SEQUENCE: 37
agccctgagg cctggagcac tgagtgaggg c 31

<210> SEQ ID NO 38
<211> LENGTH: 31
<212> TYPE: DNA
<213> ORGANISM: Artificial
<220> FEATURE:
<223> OTHER INFORMATION: oligonucleotide probe

<400> SEQUENCE: 38
agccctgagg cctggagcac tgagtgaggg g 31

```
<210> SEQ ID NO 39
<211> LENGTH: 32
<212> TYPE: DNA
<213> ORGANISM: Artificial
<220> FEATURE:
<223> OTHER INFORMATION: oligonucleotide probe

<400> SEQUENCE: 39
agccctgagg cctggagcac tgagtgaggg ga                          32

<210> SEQ ID NO 40
<211> LENGTH: 32
<212> TYPE: DNA
<213> ORGANISM: Artificial
<220> FEATURE:
<223> OTHER INFORMATION: oligonucleotide probe

<400> SEQUENCE: 40
agccctgagg cctggagcac tgagtgaggg ca                          32

<210> SEQ ID NO 41
<211> LENGTH: 30
<212> TYPE: DNA
<213> ORGANISM: Artificial
<220> FEATURE:
<223> OTHER INFORMATION: oligonucleotide probe

<400> SEQUENCE: 41
atagtcgttc ctccagggct cacagactta                             30

<210> SEQ ID NO 42
<211> LENGTH: 64
<212> TYPE: DNA
<213> ORGANISM: Artificial
<220> FEATURE:
<223> OTHER INFORMATION: exemplary indel

<400> SEQUENCE: 42
atagtcgttc ctccagggct cacagactta gactcacagg ggtcacagac tgatgaccca    60
cagg                                                                64

<210> SEQ ID NO 43
<211> LENGTH: 65
<212> TYPE: DNA
<213> ORGANISM: Artificial
<220> FEATURE:
<223> OTHER INFORMATION: exemplary indel

<400> SEQUENCE: 43
atagtcgttc ctccagggct cacagactta agactcacag gggtcacaga ctgatgaccc    60
acagg                                                                65

<210> SEQ ID NO 44
<211> LENGTH: 30
<212> TYPE: DNA
<213> ORGANISM: Artificial
<220> FEATURE:
<223> OTHER INFORMATION: oligonucleotide probe

<400> SEQUENCE: 44
tagtcgttcc tccagggctc acagactttg                             30

<210> SEQ ID NO 45
```

```
<211> LENGTH: 31
<212> TYPE: DNA
<213> ORGANISM: Artificial
<220> FEATURE:
<223> OTHER INFORMATION: oligonucleotide probe

<400> SEQUENCE: 45
tagtcgttcc tcagggctc acagacttat g                              31

<210> SEQ ID NO 46
<211> LENGTH: 63
<212> TYPE: DNA
<213> ORGANISM: Artificial
<220> FEATURE:
<223> OTHER INFORMATION: exemplary indel

<400> SEQUENCE: 46
tagtcgttcc tcagggctc acagactttg actcacaggg gtcacagact gatgacccac    60
agg                                                            63

<210> SEQ ID NO 47
<211> LENGTH: 64
<212> TYPE: DNA
<213> ORGANISM: Artificial
<220> FEATURE:
<223> OTHER INFORMATION: exemplary indel

<400> SEQUENCE: 47
tagtcgttcc tcagggctc acagacttat gactcacagg ggtcacagac tgatgaccca    60
cagg                                                           64

<210> SEQ ID NO 48
<211> LENGTH: 31
<212> TYPE: DNA
<213> ORGANISM: Artificial
<220> FEATURE:
<223> OTHER INFORMATION: oligonucleotide probe

<400> SEQUENCE: 48
ctgacagctg ccccctgctc tcctcccctg a                             31

<210> SEQ ID NO 49
<211> LENGTH: 31
<212> TYPE: DNA
<213> ORGANISM: Artificial
<220> FEATURE:
<223> OTHER INFORMATION: oligonucleotide probe

<400> SEQUENCE: 49
ctgacagctg ccccctgctc tcctcccctg c                             31

<210> SEQ ID NO 50
<211> LENGTH: 65
<212> TYPE: DNA
<213> ORGANISM: Artificial
<220> FEATURE:
<223> OTHER INFORMATION: exemplary indel

<400> SEQUENCE: 50
ctgacagctg ccccctgctc tcctcccctg ataggtagtg gcctttgcct ctctcttctt    60
catcc                                                          65

<210> SEQ ID NO 51
<211> LENGTH: 68
```

```
<212> TYPE: DNA
<213> ORGANISM: Artificial
<220> FEATURE:
<223> OTHER INFORMATION: exemplary indel

<400> SEQUENCE: 51
ctgacagctg cccctgctc tcctcccctg cccataggta gtggcctttg cctctctctt    60
cttcatcc                                                             68

<210> SEQ ID NO 52
<211> LENGTH: 31
<212> TYPE: DNA
<213> ORGANISM: Artificial
<220> FEATURE:
<223> OTHER INFORMATION: oligonucleotide probe

<400> SEQUENCE: 52
tctagaagcc aaaatgggac acagtaaaca t                                   31

<210> SEQ ID NO 53
<211> LENGTH: 31
<212> TYPE: DNA
<213> ORGANISM: Artificial
<220> FEATURE:
<223> OTHER INFORMATION: oligonucleotide probe

<400> SEQUENCE: 53
tctagaagcc aaaatgggac acagtaaaca g                                   31

<210> SEQ ID NO 54
<211> LENGTH: 64
<212> TYPE: DNA
<213> ORGANISM: Artificial
<220> FEATURE:
<223> OTHER INFORMATION: exemplary indel

<400> SEQUENCE: 54
tctagaagcc aaaatgggac acagtaaaca ttcgaatttt acttctgaac gaaatggaga    60
aact                                                                 64

<210> SEQ ID NO 55
<211> LENGTH: 66
<212> TYPE: DNA
<213> ORGANISM: Artificial
<220> FEATURE:
<223> OTHER INFORMATION: exemplary indel

<400> SEQUENCE: 55
tctagaagcc aaaatgggac acagtaaaca gattcgaatt ttacttctga acgaaatgga    60
gaaact                                                               66

<210> SEQ ID NO 56
<211> LENGTH: 31
<212> TYPE: DNA
<213> ORGANISM: Artificial
<220> FEATURE:
<223> OTHER INFORMATION: oligonucleotide probe

<400> SEQUENCE: 56
aagaacatat ctttatgttt cctgacatca g                                   31

<210> SEQ ID NO 57
<211> LENGTH: 31
<212> TYPE: DNA
```

```
<213> ORGANISM: Artificial
<220> FEATURE:
<223> OTHER INFORMATION: oligonucleotide probe

<400> SEQUENCE: 57
aagaacatat ctttatgttt cctgacatca t                               31

<210> SEQ ID NO 58
<211> LENGTH: 60
<212> TYPE: DNA
<213> ORGANISM: Artificial
<220> FEATURE:
<223> OTHER INFORMATION: exemplary indel

<400> SEQUENCE: 58
aagaacatat ctttatgttt cctgacatca gaaaaaggcc ttgagggaga aatggcttct  60

<210> SEQ ID NO 59
<211> LENGTH: 63
<212> TYPE: DNA
<213> ORGANISM: Artificial
<220> FEATURE:
<223> OTHER INFORMATION: exemplary indel

<400> SEQUENCE: 59
aagaacatat ctttatgttt cctgacatca tcagaaaaag gccttgaggg agaaatggct  60
tct                                                              63

<210> SEQ ID NO 60
<211> LENGTH: 31
<212> TYPE: DNA
<213> ORGANISM: Artificial
<220> FEATURE:
<223> OTHER INFORMATION: oligonucleotide probe

<400> SEQUENCE: 60
aatttcatac tgagaaggtt tcccaagaca t                               31

<210> SEQ ID NO 61
<211> LENGTH: 31
<212> TYPE: DNA
<213> ORGANISM: Artificial
<220> FEATURE:
<223> OTHER INFORMATION: oligonucleotide probe

<400> SEQUENCE: 61
aatttcatac tgagaaggtt tcccaagact t                               31

<210> SEQ ID NO 62
<211> LENGTH: 64
<212> TYPE: DNA
<213> ORGANISM: Artificial
<220> FEATURE:
<223> OTHER INFORMATION: exemplary indel

<400> SEQUENCE: 62
aatttcatac tgagaaggtt tcccaagaca tttcagctgc acattctgaa tgtggaagac  60
agcg                                                             64

<210> SEQ ID NO 63
<211> LENGTH: 66
<212> TYPE: DNA
<213> ORGANISM: Artificial
<220> FEATURE:
<223> OTHER INFORMATION: exemplary indel
```

<400> SEQUENCE: 63
aatttcatac tgagaaggtt tcccaagact tatttcagct gcacattctg aatgtggaag    60
acagcg                                                              66

<210> SEQ ID NO 64
<211> LENGTH: 31
<212> TYPE: DNA
<213> ORGANISM: Artificial
<220> FEATURE:
<223> OTHER INFORMATION: oligonucleotide probe

<400> SEQUENCE: 64
tccatgggca ttcttgttgt tggaggagtg t                                  31

<210> SEQ ID NO 65
<211> LENGTH: 31
<212> TYPE: DNA
<213> ORGANISM: Artificial
<220> FEATURE:
<223> OTHER INFORMATION: oligonucleotide probe

<400> SEQUENCE: 65
tccatgggca ttcttgttgt tggaggagtg g                                  31

<210> SEQ ID NO 66
<211> LENGTH: 58
<212> TYPE: DNA
<213> ORGANISM: Artificial
<220> FEATURE:
<223> OTHER INFORMATION: exemplary indel

<400> SEQUENCE: 66
tccatgggca ttcttgttgt tggaggagtg ttctgctcgg aaggtgggg gcggaggg      58

<210> SEQ ID NO 67
<211> LENGTH: 70
<212> TYPE: DNA
<213> ORGANISM: Artificial
<220> FEATURE:
<223> OTHER INFORMATION: exemplary indel

<400> SEQUENCE: 67
tccatgggca ttcttgttgt tggaggagtg gtcagtgacc agttctgctc gggaaggtgg    60
gggcggaggg                                                          70

<210> SEQ ID NO 68
<211> LENGTH: 31
<212> TYPE: DNA
<213> ORGANISM: Artificial
<220> FEATURE:
<223> OTHER INFORMATION: oligonucleotide probe

<400> SEQUENCE: 68
gccctgaggc ctggagcact gagtgagggg t                                  31

<210> SEQ ID NO 69
<211> LENGTH: 31
<212> TYPE: DNA
<213> ORGANISM: Artificial
<220> FEATURE:
<223> OTHER INFORMATION: oligonucleotide probe

<400> SEQUENCE: 69

```
gccctgaggc ctggagcact gagtgagggc a                             31

<210> SEQ ID NO 70
<211> LENGTH: 64
<212> TYPE: DNA
<213> ORGANISM: Artificial
<220> FEATURE:
<223> OTHER INFORMATION: exemplary indel

<400> SEQUENCE: 70
gccctgaggc ctggagcact gagtgagggg tgggtggctg tggaggcgcc gctctatcca   60
cagg                                                           64

<210> SEQ ID NO 71
<211> LENGTH: 66
<212> TYPE: DNA
<213> ORGANISM: Artificial
<220> FEATURE:
<223> OTHER INFORMATION: exemplary indel

<400> SEQUENCE: 71
gccctgaggc ctggagcact gagtgagggc agtgggtggc tgtggaggcg ccgctctatc   60
cacagg                                                         66

<210> SEQ ID NO 72
<211> LENGTH: 31
<212> TYPE: DNA
<213> ORGANISM: Artificial
<220> FEATURE:
<223> OTHER INFORMATION: oligonucleotide probe

<400> SEQUENCE: 72
atagtcgttc ctccagggct cacagacttt g                             31

<210> SEQ ID NO 73
<211> LENGTH: 31
<212> TYPE: DNA
<213> ORGANISM: Artificial
<220> FEATURE:
<223> OTHER INFORMATION: oligonucleotide probe

<400> SEQUENCE: 73
atagtcgttc ctccagggct cacagactta t                             31

<210> SEQ ID NO 74
<211> LENGTH: 64
<212> TYPE: DNA
<213> ORGANISM: Artificial
<220> FEATURE:
<223> OTHER INFORMATION: exemplary indel

<400> SEQUENCE: 74
atagtcgttc ctccagggct cacagacttt gactcacagg ggtcacagac tgatgaccca   60
cagg                                                           64

<210> SEQ ID NO 75
<211> LENGTH: 65
<212> TYPE: DNA
<213> ORGANISM: Artificial
<220> FEATURE:
<223> OTHER INFORMATION: exemplary indel

<400> SEQUENCE: 75
atagtcgttc ctccagggct cacagactta tgactcacag ggtcacaga ctgatgaccc    60
``` acagg 65

<210> SEQ ID NO 76
<211> LENGTH: 27
<212> TYPE: DNA
<213> ORGANISM: Artificial
<220> FEATURE:
<223> OTHER INFORMATION: oligonucleotide probe

<400> SEQUENCE: 76
cctcagttgt ggggacccca cttacgt 27

<210> SEQ ID NO 77
<211> LENGTH: 31
<212> TYPE: DNA
<213> ORGANISM: Artificial
<220> FEATURE:
<223> OTHER INFORMATION: oligonucleotide probe

<400> SEQUENCE: 77
cctcagttgt ggggacccca cttacccacc t 31

<210> SEQ ID NO 78
<211> LENGTH: 54
<212> TYPE: DNA
<213> ORGANISM: Artificial
<220> FEATURE:
<223> OTHER INFORMATION: exemplary indel

<400> SEQUENCE: 78
cctcagttgt ggggacccca cttacgtgac tagggtggtt ggcggtgaag aagc 54

<210> SEQ ID NO 79
<211> LENGTH: 63
<212> TYPE: DNA
<213> ORGANISM: Artificial
<220> FEATURE:
<223> OTHER INFORMATION: exemplary indel

<400> SEQUENCE: 79
cctcagttgt ggggacccca cttacccacc ttatgtgact agggtggttg gcggtgaaga 60
agc 63

<210> SEQ ID NO 80
<211> LENGTH: 29
<212> TYPE: DNA
<213> ORGANISM: Artificial
<220> FEATURE:
<223> OTHER INFORMATION: oligonucleotide probe

<400> SEQUENCE: 80
cctcagttgt ggggacccca cttacgtga 29

<210> SEQ ID NO 81
<211> LENGTH: 28
<212> TYPE: DNA
<213> ORGANISM: Artificial
<220> FEATURE:
<223> OTHER INFORMATION: oligonucleotide probe

<400> SEQUENCE: 81
cctcagttgt ggggacccca cttaccca 28

<210> SEQ ID NO 82

```
<211> LENGTH: 55
<212> TYPE: DNA
<213> ORGANISM: Artificial
<220> FEATURE:
<223> OTHER INFORMATION: exemplary indel

<400> SEQUENCE: 82
cctcagttgt ggggacccca cttacgtgac tagggtggtt ggcggtgaag aagcg            55

<210> SEQ ID NO 83
<211> LENGTH: 64
<212> TYPE: DNA
<213> ORGANISM: Artificial
<220> FEATURE:
<223> OTHER INFORMATION: exemplary indel

<400> SEQUENCE: 83
cctcagttgt ggggacccca cttacccacc ttatgtgact agggtggttg gcggtgaaga       60
agcg                                                                   64
```

SYSTEMS AND METHODS FOR PROBE DESIGN TO DETECT THE PRESENCE OF SIMPLE AND COMPLEX INDELS

All referenced documents and application herein and all documents referenced therein are incorporated herein by reference for all purposes. This application may be related to other patent applications and issued patents assigned to the assignee indicated above. These applications and issued patents are incorporated herein by reference to the extent allowed under applicable law.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

The invention relates to methods, algorithms, and systems for designing probes for polymorphism genotyping arrays and related technologies and to arrays or other detection systems made using the herein discussed design methods and relates to diverse fields, including genetics, genomics, biology, population biology, medicine, and medical diagnostics. In specific embodiments, the invention also relates to logic systems. In further embodiments, one or more methods may be implemented on a data handling device or system, such as a computer or other information enabled device.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

BACKGROUND OF THE INVENTION

The past years have seen a dynamic change in the ability of science to comprehend vast amount of data. Pioneering technologies such as nucleic acid arrays allow scientists to delve into the world of genetics in far greater details than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Genome-wide assays, however, must contend with the complexity of genomes; the human genome for example is estimated to have a complexity of $3\times10^9$ base pairs. Because of their abundance, single nucleotide polymorphisms (SNPs) have generally emerged as the marker of choice for genome wide association studies and genetic linkage studies.

More recently an abundance of indels have been discovered in the genome, such as within the 1000 Genomes Project. See, e.g., The 1000 Genomes Project Consortium, "An integrated map of genetic variation from 1,092 human genomes," Nature, 491, 56-65 (November 2012), which is hereby incorporated by reference in its entirety. Indels refer to the deletion (or insertion) of generally up to about 50 base pairs (bps), often 10 or less bps, at a given genomic location. Larger insertions or deletions, such as those associated with duplications, deletions, inversions and translocations that concern hundreds to thousands of bps, are usually referred to as structural variations (SVs).

Thus far, there have been few high-throughput screening methods or assays for detecting or identifying any but the most simple indels, such as single base indels. Previous work to detect more complicated indels has involved, for example, attempts to utilize next generation sequencing data for indel calls. See, e.g., Albers et al., "Dindel: Accurate indel calls from short-read data," Genome Res., 21(6): 961-973 (2011), which is hereby incorporated by reference in its entirety.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

SUMMARY

According to specific embodiments, the present invention is involved with methods and/or systems and/or devices that can be used together or independently to effect improvements in various biological detection systems.

In one aspect of the invention, computer implemented methods for selecting indel probes for distinguishing between indel alleles across a genome and useful for designing a nucleic acid probe array or other technologies are provided. According to specific embodiments, indel probes are selected that are compatible with systems and methods and software designed generally to only work on single nucleotide polymorphisms (SNPs) probes.

Nucleic acid probes targeting indels may then be determined and indels information and indel probes (and optionally interrogation bases) may be output in a computer file, a display or a printout, or transferred to a database that later may be used for designing nucleic acid probe arrays and other nucleic acid detection technology. As is known in the art, each SNP and indel may be represented by a collection of probes.

After identification of indel probes as described herein, the indels and/or probes may be are screened for performance using such criteria as performance of converted probe set and entropy based criteria. Indel probes determined or designed according to specific embodiments may be selected and an array design output that includes the indel probes.

In another aspect, collections of genotyping probes that may form an array of at least 300,000 different probes for determining the genotype of at least 300,000 SNPs and indels in a collection of SNP and indels polymorphisms are disclosed.

Software Implementations

Various embodiments of the present invention provide methods and/or systems for indel probe design can be implemented on a general purpose or special purpose information handling appliance or logic enabled system, such as a laboratory or diagnostic or production system, using a suitable programming language such as Java, C++, C#, Cobol, C, Pascal, Fortran., PL1, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Other Features & Benefits

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein.

DESCRIPTION OF SPECIFIC EMBODIMENTS

Overview

Figure 1A:
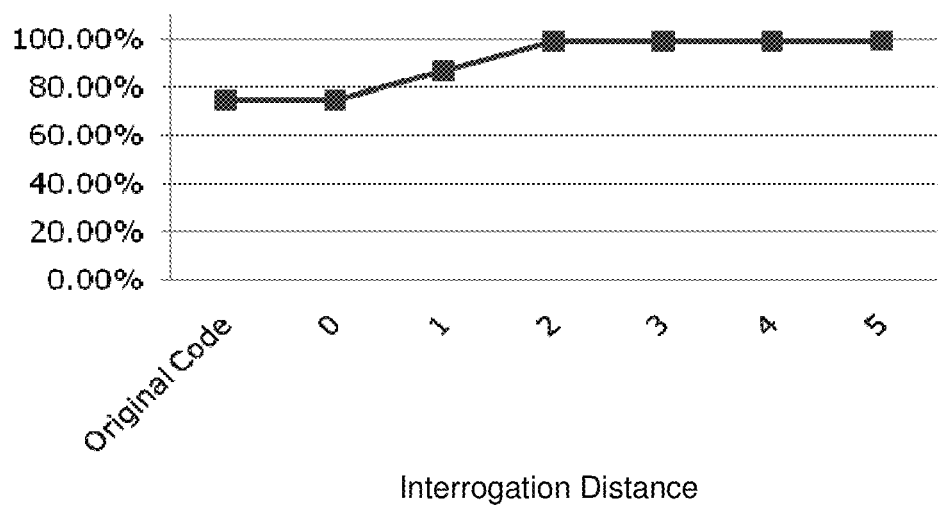
FIG. 1A-B illustrate results from an experimental probe design system according to specific embodiments of the present invention.
Figure 1B:
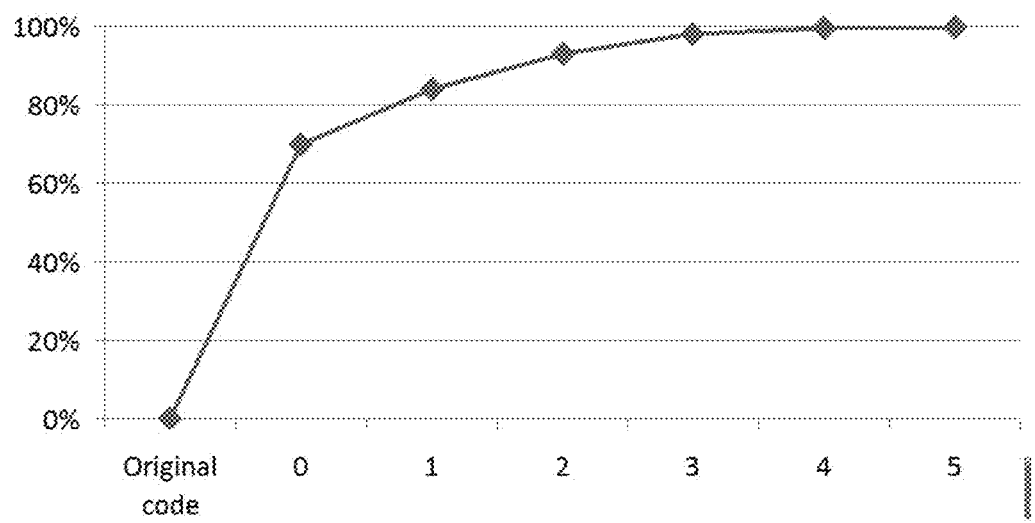

As discussed above, SNP identification has become a widely used genetic investigation tool. Increasingly, however, a need has arisen for methods for discriminating between a variety of insertion/deletion events in a genome. Standardized high-throughput methods have for the most part not been available or successful for these detections. Identifying a cost effective and accurate means for distinguishing between insertion/deletion alleles will extend the framework for new studies to identify the underlying genetic basis of complex diseases such as cancer, mental illness and diabetes.

Thus, there remains a need, however, for higher throughput, lower cost and more accurate assessments of complex and multi-base indels through the use of arrays of oligonucleotides. According to specific embodiments, methods and systems as described herein are able to detect a wide range of indels, including multi-base and complex indels, using oligonucleotide probes consistent with the current design of SNP probes in systems such as the Affymetrix® Axiom® Assay, including the Axiom® Exome Genotyping Array (Affymetrix, Inc., Santa Clara, Calif.). According to specific embodiments, a computer system or tangible digital storage media is configured with a logic routine or logic module or software application for indel-probe design that can distinguish between the presence and absence of many indels using either identical SNP-type probes with different interrogation bases or using two nearly identical SNP probes (e.g., ASO probes) followed by the same interrogation base, consistent with the current design of standard SNP probes and ASO probes in the Affymetrix Axiom system. In further embodiments, ASO probes for indels can be designed that have different interrogation bases, however this would be less compatible with some array reading and analysis software and systems.

Glossary

The term "indel" as used herein, and generally in the art, refers to a location on a genome where one or more bases are present in one allele, with no bases present in another allele. Insertions or deletions are distinct from an evolutionary point of view, but during analysis such as described herein, they are often not distinguished as an insertion in one allele is equivalent to a deletion in the other allele. Thus the term indel is to refer to the location of the insertion/deletion between two alleles.

The term "single SNP probe" or "SNP probe" as used interchangeably herein, and generally understood in the art, refers to a set of one or more probes where the probe sequence is identical. Such probes are generally identified according to their position on the array, but can also be identified by, e.g., the use of a tag sequence in a barcode fashion, detectable labels, distinguishable solid supports to which the probes are attached, or a variety of other means known in the art. Within certain assays known in the art, such as the Axiom® Assay (Affymetrix, Inc., Santa Clara, Calif.) or the Infinium® II Assay (Illumina, Inc., San Diego, Calif.), after hybridization to the sample, an interrogation base complementary to the next base in the sample sequence is added to the SNP probe (which forms a now partially double stranded complex with the sample) and a directly or indirectly detectable signal from the added interrogation base is used to determine the identity of the added interrogation base, from which the identity of the relevant allele is determined. The added interrogation base may be added by a variety of techniques known in the art, such as through ligation or single base extension. As is known in the art, certain array assays utilize SNP probes designed from either a forward or reverse perspective relative to the polymorphism and thus, during probe design, a probe can be complementary to a sequence either to the left or the right of the polymorphism.

The term "allele-specific oligonucleotide" (ASO), refers to a set of one or more probes that contains largely identical sequences, but where at least some of the probes within the set differ from other probes in the set by one or more bases. The different alleles that are interrogated by a set of probes in this case are generally measured according to the location on the array where each ASO is placed, or by an alternative technique known in the art to identify and distinguish one type of probe within the array from another probe.

The term "interrogation base" refers to the base in the assay that will be selectively added to a hybridized probe, such as a SNP probe or ASO, and provide a complement to the next base in the sample sequence. Interrogation bases are either directly labeled, or indirectly labeled after they are added so that the resulting signal indicates a particular allele. Interrogation bases may be added by any means known in the art that requires the interrogation base to be complementary to the nucleic acid hybridized with the probe, such as through ligation or single base extension.

The term "detection channel" refers to a channel within an assay system that utilizes a particular label, with the resulting signal being used for identifying alleles. In many current systems, only two channels are used (e.g., where each of the two channels has its own distinguishable label), even though there are four possible interrogation bases for each hybridized probe. In other systems, four channels are used such that each of the four possible interrogation bases is associated with a distinct label.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to beads (such as silica or resin beads), silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations. In addition to SNPs, genotyping can also be performed with respect to detection of various indels within an individual's genome.

A "genetic map" is a map that presents the order of specific sequences on a chromosome. A genetic map expresses the positions of genes relative to each other without a physical anchor on the chromosome. The distance between markers is typically determined by the frequency of recombination, which is related to the relative distance between markers. Genetic map distances are typically expressed as recombination units or centimorgans (cM). The physical map gives the position of a marker and its distance from other genes or markers on the same chromosome in base pairs and related to given positions along the chromosome. See, Color Atlas of Genetics, Ed. Passarge, Thieme, New York, N.Y. (2001), which is incorporated by reference. Genetic variation refers to variation in the sequence of the same region between two or more individuals.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above.

The terms "hybridization probe" or "probe" as used interchangeably herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. In particular applications, the term "probe" refers to a surface-immobilized molecule that can be recognized by a particular target. Examples of probes that can include indel related probes as described herein are generally oligonucleotides.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "label" as used herein refers to a moiety that directly or indirectly facilitates detection of a molecule by providing a detectable signal. Common labels include fluorescent, luminescent, light-scattering, and/or colorimetric labels. Suitable labels include fluorescent moieties, as well as radionuclides, enzymes, substrates, cofactors, inhibitors, chemiluminescent moieties, and the like. A label can be applied directly to a label target, or indirectly through the use of two or more sets of molecules (e.g., a labeling scheme that utilizes biotin, a florescent label conjugated to streptavidin, and biotinylated anti-streptavidin antibodies).

The term "mapping array" refers in general to an array that interrogates a collection of more than about 10,000 polymorphisms, preferably single nucleotide polymorphisms. In a preferred aspect a mapping array interrogates the genotype of a collection of SNPs that are representative of a genome. For example, a mapping array may be designed to interrogate a collection of SNPs selected to that the SNPs are preferably spaced throughout the genome so that all non-repetitive regions of the genome are within a specified distance of at least one SNP in the collection. This allows the genome to be interrogated by the mapping array in linkage and association studies so that genomic regions that are associated or linked with a phenotype of interest may be identified. For a discussion of methods for using SNPs to test associations of SNPs and haplotypes with complex traits see, for example, D. Schaid (2006) *Ann Hum Genet.* 70:116-30 and D. Schaid Genetic Epidemiol 27:34-364 (2004). Examples of mapping arrays include the Affymetrix Mapping 10K, Mapping 100K and Mapping 500K arrays and array sets. These mapping arrays are a type of genotyping array because the output is the genotype of a plurality of polymorphisms. Mapping arrays are also described, for example, in US Patent Publication Nos. 20060024715, 200502227244 and 20040146890. Methods of using mapping arrays are also disclosed in Matsuzaki et al., Nat Methods 1:109-11 (2004). Mapping arrays may also interrogate a collection of indels in addition to SNPs.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligonucleotides tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, uracil, adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The terms "oligonucleotide" or "polynucleotide," as used interchangeably herein refer to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix.

The term "polymorphism" as used herein refers to the occurrence of two or more genetically determined alternative sequences or alleles in a population. A polymorphic marker or site is the locus at which divergence occurs. Preferred markers have at least two alleles, generally each occurring at frequency of greater than about 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. Single nucleotide polymorphisms (SNPs) are included in polymorphisms. Single nucleotide polymorphisms (SNPs) are positions at which two alternative bases occur at appreciable frequency (generally >1%) in a given population. SNPs are the most common type of human genetic variation. A polymorphic site is frequently preceded by and followed by highly conserved sequences (e.g., sequences that vary in less than 1/100 or 1/1000 members of the populations). A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to various embodiments, the solid support(s) will take the form of wafers, chips, beads, resins, gels, microspheres, microparticles, slides or other geometric configurations.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as antiprobes. As the term targets is used herein, no difference in meaning is intended. A "Probe Target Pair" is formed when two macromolecules have combined through molecular recognition to form a complex.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention therefore relates to diverse fields impacted by the nature of molecular interaction, including chemistry, biology, medicine and diagnostics. The ability to do so would be advantageous in settings in which large amounts of information are required quickly, such as in clinical diagnostic laboratories or in large-scale undertakings such as genomic projects relating to various organisms and diseases that analyze hundreds to thousands of individuals.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Introduction

A variety of techniques are known for the manufacture and use of oligonucleotide arrays, such as the techniques disclosed within, e.g., U.S. Pat. No. 5,143,854 to Pirrung et al.; U.S. Pat. No. 5,744,305 to Fodor et al.; U.S. Pat. No. 7,332,273 to Trulson et al.; U.S. Pat. Nos. 5,945,334 and 6,140,044 to Besemer et al.; U.S. Pat. No. 5,545,531 to Rava et al.; U.S. Pat. No. 6,660,233 to Coassin et al.; U.S. Patent Application Publication Nos. 2004/0038388 and 2006/0088863 to Yamamoto et al.; U.S. Patent Application Publication No. 2005/0023672 to Oostman et al.; U.S. Patent Application Publication No. 2008/0003667 to Jones et al.; U.S. Patent Application Publication Nos. 2006/0246576, 2006/0234371, 2011/0136699 and 2010/0248981 to Shirazi; pending U.S. patent application Ser. No. 13/157,268, filed Jun. 9, 2011; U.S. Pat. No. 6,242,266 to Schleifer et al.; U.S. Pat. No. 6,375,903 to Cerrina et al.; U.S. Pat. No. 5,436,327 to Southern et al.; U.S. Pat. No. 5,474,796 to Brennan; U.S. Pat. No. 5,658,802 to Hayes et al.; U.S. Pat. No. 5,770,151 to Roach et al.; U.S. Pat. No. 5,807,522 to Brown et al.; U.S. Pat. No. 5,981,733 to Gamble et al.; U.S. Pat. No. 6,101,946 to Martinsky; U.S. Pat. Nos. 6,355,431 and 6,429,027 to Chee et al.; U.S. Pat. No. 7,510,841 to Stuelpnagel et al., U.S. Pat. Nos. 7,745,091 and 7,745,092 to True; U.S. Patent Application Publication No. 2010/0297448 to True et al.; and U.S. Patent Application Publication Nos. 2010/0227279, 2010/0227770 and 2009/0149340 to True, all of which are expressly incorporated herein by reference for all purposes. Arrays according to the referenced techniques have been widely commercialized, such as Affymetrix® arrays (Affymetrix, Inc., Santa Clara, Calif.) in the form of GeneChip® array cartridges, peg array strips, and Axiom® peg array plates, Illumina® BeadArray® arrays (Illumina, Inc., San Diego, Calif.), and Agilent® SurePrint® arrays (Agilent Technologies, Inc., Santa Clara, Calif.).

Indel Probe Design

Logic routines for the determination of SNP probes that can be used in various DNA analysis systems have long existed. Previous arrays designed to interrogate SNPs would commonly utilize probe sets that contained a probe that was perfectly complementary to a target of interest (including the SNP of interest) and one or more other probes which contained one or more monosubstitutions as compared to the perfectly complementary probe. The resulting intensity data for the different probes in the probe set would then be compared to produce a genotype call for the SNP of interest. See, e.g., U.S. Pat. No. 5,858,659, which is hereby incorporated herein by reference in its entirety.

More recent arrays for genotyping SNPs include Axiom® Arrays (Affymetrix, Inc., Santa Clara, Calif.) and Infinium® II Arrays (Illumina, Inc., San Diego, Calif.). These arrays utilize a SNP probe that is complementary to a sequence that flanks the SNP site within the target nucleic acid of interest, and thus the SNP probe in these arrays does not directly hybridize with the target nucleic acid at the SNP site. Instead, the double-stranded portion of the probe-target duplex ends immediately upstream of the SNP. Interrogation of the SNP site is then accomplished by the addition of a nucleotide or probe (with the nucleotide or probe comprising one of two different haptens) to one end of the SNP probe (e.g., 5',3') through an appropriate mechanism known in the art that requires complementarity to the base of the target at the SNP site (e.g., ligation or single base extension). Determination of what allele was present at the SNP site is ascertained through subsequent detection of the particular hapten associated with the nucleotide or probe that was added.

The Axiom® Assay utilizes 30-base oligonucleotide SNP probes in a two color format. The identity of the base at the SNP site is ascertained by the ligation of probes containing one of two haptens that serve as attachment sites for one of two fluorescent labels, depending the identity of the base to the ligated to the SNP probe (e.g., a first hapten/label combination is associated with probes that will ligate when the SNP site is A or T, and a second hapten/label combination is associated with probes that will ligate when the SNP site is C or G). See, e.g., Hoffmann et al., "Next generation genome-wide association tool: design and coverage of a high-throughput European-optimized SNP array," Genomics, 98(2): 79-89 (2011); and Hoffmann et al., "Design and coverage of high throughput genotyping arrays optimized for individuals of East Asian, African American, and Latino race/ethnicity using imputation and a novel hybrid SNP selection algorithm," Genomics, 98(6): 422-30 (2011), both of which are hereby incorporated by reference in their entireties.

The Infinium® II Assay utilizes 50-base oligonucleotide SNP probes in a two color format. The identity of the base at the SNP site is ascertained by the incorporation of ddNTPs bearing one of two different haptens through single base extension of the SNP probe, with each hapten associated with a different fluorescent label (e.g., ddCTP and ddGTP are associated with a first hapten/label combination while ddATP and ddTTP are associated with a second hapten/label combination). See, e.g., Gunderson et al., "Whole-genome genotyping of haplotype tag single nucleotide polymorphisms," Pharmacogenomics, 7(4): 641-8 (2006); and Steemers et al., "Whole-genome genotyping with the single-base extension assay," Nature Methods, 3: 31-33 (2006), both of which are hereby incorporated by reference in their entireties.

In general, earlier probe design logic routines, both for the Axiom family and others, had a number of limitations that made them unsuitable for designing effective probes for indels. Among the common restrictions where:

Probes could be designed for only biallelic (only two different bases at the polymorphic position) SNPs and for some single-base indels as described below.

Probes could not be designed for multi-base indels, e.g., –/CAG, –/AA

Probes could not be designed for complex indels, e.g., A/CG, TT/CGG

Allele Specific Oligo (ASO) probes could not be designed for various indels, e.g., Homo-polymer runs: ATGACT-GACGGTT[–/A]AACTATCACTCG (SEQ ID NO:1 (–), SEQ ID NO:2 (A)); where the interrogation bases are in same channel:

TACGCAGATCAGC[–/G]CACGTACTTCGG (SEQ ID NO:3 (–), SEQ ID NO:4 (G)), where in this example the interrogation base is either G (no deletion) or C (deletion) and where only two channels are used in the assay, and thus only two different labels are used, with a first one for A or T and a second one for C or G.

While earlier SNP probe design methods could identify some indels, in general, even these had several restrictions. The only single base insertions that could be addressed where those for which either a) the deleted base was either A or T and the base after the deletion was a G or C or b) the deleted based was either G or C and the base after the deletion was a A or T. In the above two cases the probe design followed the design for the most common type of SNP where the interrogation base distinguishes between two events. Event 1 is (A or T) and event 2 is (G or C) (or vice versa).

Methods and systems as described herein significantly extend the number of indels for which probes can be designed via an automated process. One difficulty addressed according to specific embodiments is illustrated be shown in the following 2 simple examples (sometimes a combination of both). The deleted bases are shown in brackets ([..]).

EXAMPLE 1

```
                    SEQ ID NO: 5 (-), SEQ ID NO: 6 (TCA)
         CCCTTGGAGCCAGGG[-/TCA]

TCGTTGAGACCAGGTAAGCCAGGAGGTCCCTAAAT
```

It appears at first that no single base can distinguish between the presence and absence of the indel, as the first base of the deletion "T" is equal to the first base following the deletion. (Shown in bold). Hence a probe ending in "CCCTTGGAGCCAGGG" (residues 1-15 of SEQ ID NOs:5 and 6) cannot be used. However, according to specific embodiments in this case the indel "event" can be rewritten equivalently in a way that eliminates the issue. The above indel is equivalent to the following event:

```
                    SEQ ID NO: 5 (-), SEQ ID NO: 6 (TCA)
    CCCTTGGAGCCAGGGTC[-/ATC]

GTTGAGACCAGGTAAGCCAGGAGGTCCCTAAAT
```

Because, the first base "T" of the [–/TCA] indel was equal to the first base "T" to the right after the indel (e.g., TCGT...) a probe sequence used to identify the indel can be shifted downstream (in this instance, given the initial probe sequence ending in "CCCTTGGAGCCAGGG" (residues 1-15 of SEQ ID NOs:5 and 6), a shift to the right) until the base after the indel identification sequence (e.g., "G") differs from the first base of the indel.

EXAMPLE 2

```
                            SEQ ID NO: 7 (-), SEQ ID NO: 8 (CA)
    CCTGAGGCCTGGAGCACTGAGTGAGGG[-/CA]GAGGGTGGCTGTGGAGGCGCCGCTCTA
```

The first base of the indel differs from the first base after the indel, but the bases are indistinguishable given the characteristics of the assay at issue (e.g., the number and configuration of the detection channels). For example, if the assay at issue is a two channel assay that has a first label used when the interrogation base is an A or T and a second label when the interrogation base is a G or C, then if the first base of the indel is C, it is indistinguishable from when the first base after the indel is a G, as is the case here. Because within this assay, the interrogation base can only be differentiated between {A or T} versus {G or C}, two Allele Specific Oligonucleotides (ASO) are designed, one that includes the "C" and the other one that includes the "G".

According to specific embodiments, to optimize data consistency from the resulting signals from the labels used within a particular assay, it is preferred that the ??interrogation??base following the two ASO probes is the same to ensure that the same interrogation base is added and the same type of label is detected for each of the two ASO probes. This will typically only be true in 25% of the cases. According to specific embodiments, if the bases differ, one of the probes is shifted downstream (left or right as is applicable based on which flanking side of the indel is at issue), thus adding an additional base to the ASO at the downstream end and removing a base from the ASO at its upstream end, and so forth until the interrogation bases are equal. Each addition of a base to the ASO (shifting the probe right or the left) moves the interrogation base away from the polymorphisms in the ASO probes that identify the indel insertion and deletion alleles. The distance of the interrogation base from the polymorphisms is referred to herein as in the interrogation distance, and the maximum amount of allowed distance is the interrogation distance threshold. In specific embodiments, each addition of a base is repeated up to 5 times in one specific embodiment, or, in other words, the interrogation distance threshold in this embodiment is 5. When the interrogation distance threshold is exceeded, the indel is not designed. With an interrogation distance threshold of 5, experiments have demonstrated that using this approach almost all indels encountered can be represented by a probe designed using one or more methods as described herein. However, it is not required the interrogation base for two ASO probes be the same, as other embodiments include the design of ASO probes that have differing interrogation bases. This flexibility can be useful to permit interrogation of a particular indel event in situations such as, for example, the interrogation distance threshold is selected to be a smaller quantity, such as 2 as opposed to 5.

According to specific embodiments, an example methodology proceeds as described below. Specific example oligonucleotides are provided for demonstration purposes. As will be understood in the art, oligonucleotide probes can generally be sequences to the left or to the right of a polymorphism that is being detected. Also, as understood in the art, each sequence described herein shall be understood to include its complement unless the context requires otherwise. Because samples generally are derived from double stranded DNA or similar, a probe of either complement can generally detect the polymorphism. As is further understood in the art, in the context of array based genotyping systems, a single "probe" generally is one or more copies of an identical unpaired oligonucleotide. Detection of a particular polymorphism occurs when that probe binds to its complement in the sample and then an interrogation base is added to the probe just adjacent to the probe/sample hybridization. The interrogation base effectively is the complement of usually a single varying nucleotide that would be next in the sequence, however in certain assay systems such as the Axiom® Assay, the interrogation base generally is provided at the 3' end on an a oligonucleotide of several bases (e.g., 6 bases, or a hexamer) and in an assay, each interrogation base is available with every possible additional sequence attached for the remainder of the oligonucleotide, or with the remainder of the oligonucleotide utilizing universal or degenerate bases, or other similar approaches known in the art. In some array based genotyping systems, probes are bound to a solid support (such as to a silica chip, a bead, or other substrate) attached by the end furthest away from the site of interrogation base attachment and the interrogation bases are free in solution. For ease of reference, probe sequences are presented below in plain text. Interrogation bases are presented in bold underlined text. For standard SNPs, the interrogation base is generally always the polymorphism. As will be understood in the art, polymorphisms are indicated in square brackets, with a slash between the two forms or alleles of the polymorphism, e.g., [A/C] or [AG/CCC]. A minus sign "–" is used to indicate a deletion polymorphism, e.g., [–/CAC].

An example method according to specific embodiments proceeds using one or more steps as described below. Illustrative example sequences are provided below each option. Note that in various systems, as is known in the art, probes "on the right" of a SNP must be reverse-complimented to be in the same paradigm as the probes "on the left" of a SNP. Probes presented here are representations of the actual probe sequences on the array, which may be reversed or complemented as needed as will be understood in the art. The first three examples represent probes designed by existing methods:

1. For standard SNP's, probes are designed as done previously, such as in:

```
                                                         SEQ ID NO: 9
CTTGGCACAGTCTAGACATCTCAAACTGCT (left probe)

SEQ ID NO: 10 (A), SEQ ID NO: 11 (C)
CTTGGCACAGTCTAGACATCTCAAACTGCT[A/C]TACTATGGGGCAAGACCCCTGGACCACCCAACCAC

SEQ ID NO: 12
(right probe) TACTATGGGGCAAGACCCCTGGACCACCCA
```

2. For standard SNP's that require ASO probes, ASO probes are also designed as done previously, such as in:

```
                                                         SEQ ID NO: 13
GGCTTCTAGATGGAATCAGCAGCGGAAAACA (left ASO probes)

SEQ ID NO: 14
GGCTTCTAGATGGAATCAGCAGCGGAAAAGA

SEQ ID NO: 15 (C), SEQ ID NO: 16 (G)
GGCTTCTAGATGGAATCAGCAGCGGAAAA[C/G]AACAGGAAGAGATGAAGAAGCAAAATCAACAAGAC

SEQ ID NO: 17
(right ASO probes) ACAACAGGAAGAGATGAAGAAGCAAAATCAA

SEQ ID NO: 18
AGAACAGGAAGAGATGAAGAAGCAAAATCAA
```

3. Probes for indels meeting very specific criteria are designed as done previously. In this case, the interrogation base will be either (A or T) for the deletion and C for the insertion, such as in:

```
                                                         SEQ ID NO: 19
TTATATAGAAAGGCTCTAAGTACCTTGGGTA (left deletion)

SEQ ID NO: 20
TTATATAGAAAGGCTCTAAGTACCTTGGGTC (left insertion)

SEQ ID NO: 21 (-), SEQ ID NO: 22 (C)
TTATATAGAAAGGCTCTAAGTACCTTGGGT[-/C]ATGTAAAGGTGGCCTGAAGACTGCCAGAAG

SEQ ID NO: 23
(right deletion) TATGTAAAGGTGGCCTGAAGACTGCCAGAAG

SEQ ID NO: 24
(right insertion) CATGTAAAGGTGGCCTGAAGACTGCCAGAAG
```

According to specific embodiments, the limitations on probe design for indels are overcome by including the following additional probe design options:

4. Start with probe to either flanking side (e.g., the left or alternatively to the right) of the indel alleles and compare the interrogation bases of the deletion and the insertion. If the interrogation bases are different (e.g., "T" and "C" below) and in different channels (e.g., where the channels are A/T and C/G), design a single probe using the interrogation bases (e.g., "T" and "C" below) to differentiate such as in:

```
                                                         SEQ ID NO: 25
ATTCTCACCTTTTCACCCTTGGAGCCAGGG

SEQ ID NO: 26 (-), SEQ ID NO: 27 (TCA)
ATTCTCACCTTTTCACCCTTGGAGCCAGGG[-/TCA]CCTTTGAGACCAGGTAAGCCAGGAGGTCCCTAAAT
```

5. If the interrogation bases are the same (e.g., A and A below), slide one base downstream and retry:

Original, with (A,A) as the interrogation bases:

```
                                                                SEQ ID NO: 28
CTCTAGAAGCCAAAATGGGACACAGTAAAC

SEQ ID NO: 29 (-), SEQ ID NO: 30 (AG)
CCTCTAGAAGCCAAAATGGGACACAGTAAAC[-/AG]ATTCGAATTTTACTTCTGAACGAAATGGAGAAACT
```

Moved one downstream, with (G,T) now the interrogation bases:

```
                                                                SEQ ID NO: 31
TCTAGAAGCCAAAATGGGACACAGTAAACA  (insertion and deletion probe)

SEQ ID NO: 32 (-), SEQ ID NO: 33 (AG)
TCTAGAAGCCAAAATGGGACACAGTAAAC[-/AG]ATTCGAATTTTACTTCTGAACGAAATGGAGAAACT
```

6. If the interrogation bases are different and in the same channel, design allele-specific oligonucleotides (ASO) to differentiate:
Original, with (C,G) as the interrogation bases:

```
                                                                SEQ ID NO: 34
AGCCCTGAGGCCTGGAGCACTGAGTGAGGG

SEQ ID NO: 35 (-), SEQ ID NO: 36 (CA)
AGCCCTGAGGCCTGGAGCACTGAGTGAGGG[-/CA]GAGGGTGGCTGTGGAGGCGCCGCTCTATCCACAGG
```

Slide one base downstream and incorporate the previous interrogation base into each ASO probe:

Slide one base downstream the probe that measures the insertion until an identical interrogation base is found:

```
                         SEQ ID NO: 37
AGCCCTGAGGCCTGGAGCACTGAGTGAGGGC (insertion)

SEQ ID NO: 38
AGCCCTGAGGCCTGGAGCACTGAGTGAGGGG (deletion)
```

```
                         SEQ ID NO: 40
AGCCCTGAGGCCTGGAGCACTGAGTGAGGGCA
```

Identify the new interrogation base for the probe that measures the deletion:

7. If no nearby identical interrogation base can be found, slide deletion (or insertion) probe one base downstream and retry, for a number of times until a threshold is exceeded.

The methods and systems as described herein enable successful "standard" SNP or ASO probe design for a wide range of indels that were previously not detectable using previous genotyping arrays as discussed herein. A number of examples are provided below:

```
                         SEQ ID NO: 39
AGCCCTGAGGCCTGGAGCACTGAGTGAGGGA
```

Examples of Indel Probes that were Previously not Designed:

```
                                                                SEQ ID NO: 41
ATAGTCGTTCCTCCAGGGCTCACAGACTTA (adds G for [-] and A for [A])

SEQ ID NO: 42 (-), SEQ ID NO: 43 (A)
ATAGTCGTTCCTCCAGGGCTCACAGACTT[-/A]AGACTCACAGGGGTCACAGACTGATGACCCACAGG

SEQ ID NO: 44
TAGTCGTTCCTCCAGGGCTCACAGACTTT (G) Deletion probe

SEQ ID NO: 45
TAGTCGTTCCTCCAGGGCTCACAGACTTAT (G) Insertion probe

SEQ ID NO: 46 (-), SEQ ID NO: 47 (A)
TAGTCGTTCCTCCAGGGCTCACAGACTT[-/A]TGACTCACAGGGGTCACAGACTGATGACCCACAGG
```

Differentiate multibase indels by addition of interrogation base in different channels:

```
                                      SEQ ID NO: 48 (A), SEQ ID NO: 49 (C)
CTGACAGCTGCCCCCTGCTCTCCTCCCCTG[A/C] Probe SEQ ID NO: 50 (-), SEQ ID NO: 51 (CCC)
CTGACAGCTGCCCCCTGCTCTCCTCCCCTG[-/CCC]ATAGGTAGTGGCCTTTGCCTCTCTCTTCTTCATCC
```

Differentiate multibase indels where first base is included in probe by addition of interrogation base in different channels:

SEQ ID NO: 52 (T), SEQ ID NO: 53 (G)
TCTAGAAGCCAAAATGGGACACAGTAAACA[T/G] Probe SEQ ID NO: 54 (-), SEQ ID NO: 55 (AG)
TCTAGAAGCCAAAATGGGACACAGTAAAC[-/AG]ATTCGAATTTTACTTCTGAACGAAATGGAGAAACT Differentiate multibase indels by including entire indel and by addition of interrogation base in different channels:

SEQ ID NO: 56 (G), SEQ ID NO: 57 (T)
AAGAACATATCTTTATGTTTCCTGACATCA[G/T] Probe SEQ ID NO: 58 (-), SEQ ID NO: 59 (CAT)
AAGAACATATCTTTATGTTTCCTGA[-/CAT]CATCAGAAAAAGGCCTTGAGGGAGAAATGGCTTCT Allele-specific probes differentiate multibase indels SEQ ID NO: 60
AATTTCATACTGAGAAGGTTTCCCAAGACA(T) Deletion probe SEQ ID NO: 61
AATTTCATACTGAGAAGGTTTCCCAAGACT(T) Insertion probe SEQ ID NO: 62 (-), SEQ ID NO: 63 (TT)
AATTTCATACTGAGAAGGTTTCCCAAGAC[-/TT]ATTTCAGCTGCACATTCTGAATGTGGAAGACAGCG Probes can differentiate multibase indels that are quite large

SEQ ID NO: 64 (T), SEQ ID NO: 65 (G)
TCCATGGGCATTCTTGTTGTTGGAGGAGTG[T/G]

SEQ ID NO: 66 (-), SEQ ID NO: 67 (GGTCAGTGACCA)
TCCATGGGCATTCTTGTTGTTGGAGGAGT[-/GGTCAGTGACCA]GTTCTGCTCGGGAAGGTGGGGGCGGAGGG

Design Considerations

According to specific embodiments, probe sets using the above methods can be designed from either flanking side (left or right, as in SNP design tools). One assumed design principle according to specific embodiments for specific systems is that ASO probes will work best if interrogating the same base (e.g., same channel, so dye/base effects cause less cluster scatter). According to specific embodiments, another assumed design principle is that ASO probes will work best if their sequences are most similar (e.g., fewer probe-sequence-specific effects causing cluster scatter.) According to specific embodiments, another assumed design principle is that ASO probes will work best if differing only in the bases as close to the interrogation site as possible. If the interrogation site has drifted too far from the SNP, the probe set from that direction is generally rejected. For ASO probe sets, the effective interrogation distance is generally taken as the greater of the two probes. According to specific embodiments, the probes in an array design are generally all designed to the same length (e.g., all are 30-mers or 50-mers) as will be understood in the art in order to provide more uniform hybridization kinetics for the array. According to specific embodiments, probes designed by methods described herein are kept at the same length even if particular indel related probes are designed such that the interrogation base has shifted one or more bases downstream. In the text examples provided here, sequences away from the ligation base are deleted for ease of reading.

Results

According to specific embodiments, in one example experimental test design system, the methods discussed above improved recovery rate from 75 to 99% for single base indels and also improved recovery rate from 0 to 100% for multiple base indels. A substantial majority of indels are recovered by allowing up to 3 bases of interrogation distance.

Other Embodiments

According to specific embodiments, the above methods described herein restricted probe design to remain backwards compatible with various existing SNP detection systems and methods. Some of the methods above were selected to reduce software modifications to existing SNP probe design systems. If this final requirement is lifted, however, according to other specific embodiments, more flexibility can be achieved in indel probe design.

As one example, specific embodiments may use differing interrogation bases for ASO probes. To minimize labeling effects or scanning effects for some prior systems and stay in the same channel, the method can search for either interrogation base in the same channel when comparing interrogation bases between the deletion probe and the insertion probe. This allows some previously undesignable probes and allows some probes with shorter interrogation distances. For example:

```
                                                                SEQ ID NO: 68
GCCCTGAGGCCTGGAGCACTGAGTGAGGGG(T) Deletion probe SEQ ID NO: 69
GCCCTGAGGCCTGGAGCACTGAGTGAGGGC(A) Insertion probe SEQ ID NO: 70 (-), SEQ ID NO: 71 (CA)
GCCCTGAGGCCTGGAGCACTGAGTGAGGG[-/CA]GTGGGTGGCTGTGGAGGCGCCGCTCTATCCACAGG
```

In further specific embodiments any interrogation base can be allowed when comparing interrogation bases, effectively requiring only the addition of a single additional base into the ASO probe for both the deletion and the insertion probe when compared to the standard probe. For example:

descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from

```
                                                                SEQ ID NO: 72
ATAGTCGTTCCTCCAGGGCTCACAGACTTT(G) Deletion probe (interrogation base)

SEQ ID NO: 73
ATAGTCGTTCCTCCAGGGCTCACAGACTTA(T) Insertion probe (interrogation base)

SEQ ID NO: 74 (-), SEQ ID NO: 75 (A)
ATAGTCGTTCCTCCAGGGCTCACAGACTT[-/A]TGACTCACAGGGGTCACAGACTGATGACCCACAGG
```

Finding the Optimal ASO Probe Pairs (Minimize Ligation Distance)

According to specific embodiments discussed above, the deletion probe is prioritized for determining the interrogation base. If a corresponding match is found for the insertion probe, the method ends. However, sometimes a better pair of probes can be found such that the difference between the probes is minimized. For example:

Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3$^{rd}$ Ed., W.H. Freeman Pub., New York, N.Y. and Berg et al. (2002) Biochemistry, 5th Ed., W.H. Freeman Pub., New York, N.Y., all of which are herein incorporated in their entirety by reference for all purposes.

```
                                                                SEQ ID NO: 76
CCTCAGTTGTGGGGACCCCACTTACG(T) Deletion probe SEQ ID NO: 77
CCTCAGTTGTGGGGACCCCACTTACCCACC(T) Insertion probe SEQ ID NO: 78 (-), SEQ ID NO: 79 (CCACCTTAT)
CCTCAGTTGTGGGGACCCCACTTAC[-/CCACCTTAT]GTGACTAGGGTGGTTGGCGGTGAAGAAGC
```

According to specific embodiments, to minimize the interrogation distance difference between the two probes, the method can search for an insertion probe starting at the SNP position. For example:

The present invention can employ solid substrates, including arrays in some preferred embodiments. Methods and techniques applicable to polymer (including protein) array synthesis have been described in U.S. Ser. No. 09/536,841,

```
                                                                SEQ ID NO: 80
CCTCAGTTGTGGGGACCCCACTTACGTG(A) Deletion probe SEQ ID NO: 81
CCTCAGTTGTGGGGACCCCACTTACCC(A) Insertion probe SEQ ID NO: 82 (-), SEQ ID NO: 83 (CCACCTAT)
CCTCAGTTGTGGGGACCCCACTTAC[-/CCACCTTAT]GTGACTAGGGTGGTTGGCGGTGAAGAAGCG
```

Devices, Systems and Methods

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid detection systems that are useful in the present invention include those that are commercially available from Affymetrix (Santa Clara, Calif.) under the brand names GeneChip® and Axiom®. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361, 947, 6,368,799 and 6,333,179. Other uses are embodied in U.S. Pat. Nos. 5,871,928, 5,902,723, 6,045,996, 5,541,061, and 6,197,506.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389,194 (U.S. Patent Application Publication 20040012676), 60/493, 495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Given the millions of SNPs that are estimated to exist and the large subset already in databases, there is a need to prune this number down to a number that will fit on a few microarrays at current feature sizes. Applications of microarray for SNP genotyping have been described in e.g., a number of U.S. patents and patent applications, including U.S. Pat. Nos. 6,300,063, 6,361,947, 6,368,799 U.S. patent application Ser. No. 11/075,121, and 10/442,021 and US Patent Publication Nos. 20040067493, 20030232353, 20030186279, and 20030186280, all incorporated herein by reference in their entireties for all purposes. Methods and arrays for simultaneous genotyping of more than 10,000 and more than 100,000 SNPs have also been described for example in Kennedy et al. (2003) Nat. Biotech. 21:1233-7, Matsuzaki et al., (2004) Genome Res. 14(3): 414-425, and Matsuzaki et al (2004) Nature Methods, Vol 1, 109-111, all incorporated herein by reference in their entireties for all purposes. Despite the massive amounts of data and detection technologies available for SNPs, it has been increasingly realized that many important polymorphisms may not be SNPs, but may include insertions or deletions.

In one aspect of the invention, computer software products and computer systems are provided to perform the methods (algorithms) described above. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Computer systems of the invention typically include at least one CPU coupled to a memory. The systems are configured to store and/or execute the computerized methods described above. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Methods of Use

The methods of the presently claimed invention can be used for a wide variety of applications including, for example, linkage and association studies, identification of candidate gene regions, genotyping clinical populations, correlation of genotype information to phenotype information, loss of heterozygosity analysis, and identification of the source of an organism or sample, or the population from which an organism or sample originates. Any analysis of genomic DNA may be benefited by a reproducible method of polymorphism analysis. Furthermore, the probes, sequences, arrays and collections of SNPs and indels and indel probes of the presently claimed invention are particularly well suited for study and characterization of extremely large regions of genomic DNA in individual samples and in populations.

Correlation of Polymorphisms with Phenotypic Traits

While much of human and other organisms sequence variation is attributable to or correlated with SNPs, an important portion is attributable to insertions or deletions (indels) of one or more bases. Repeat length polymorphisms and rearrangements are other sources of sequence variation. On average, SNPs occur every 1,000-2,000 bases when two human chromosomes are compared, resulting in an estimated 3,000,000 SNPs in the human genome. (See, The International SNP Map Working Group, *Science* 409: 928-933 (2001) incorporated herein by reference in its entirety for all purposes.) Human diversity is limited not only by the number of SNPs occurring in the genome but further by the observation that specific combinations of alleles are found at closely linked sites, generating haplotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

Correlation of individual polymorphisms or groups of polymorphisms with phenotypic characteristics is a valuable tool in the effort to identify DNA variation that contributes to population variation in phenotypic traits. Phenotypic traits include, for example, physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic. Large scale association studies using large groups of SNPs and indels further enhanced with detections for indels provides additional tools for disease association studies.

Many diseases may correlate with multiple genetic changes making identification of the polymorphisms associated with a given disease more difficult, particularly when identification is limited to SNPs. One approach to overcome this difficulty is to systematically explore the limited set of common gene variants for association with disease. To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. Using the methods as taught herein, gene arrays can distinguish a larger set of non-SNP polymorphisms, some of which may be particularly important markers for particular diseases. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

High density genotyping arrays have recently been used to identify polymorphisms associated with disease. See, for example, Klein et al. *Science,* 1109557, 2005, Butcher et al., *Behav Genet* 34(5), 549-55 (2004), Gissen et al., *Nat. Genet.* 36(4):400-4 (2004), and Puffenberger et al, PNAS 101: 11689-94. High density genotyping arrays have also been used to identify regions of genomic amplification, deletion, loss of heterozygosity and allelic imbalance. See, for example, Cox, et al., *PNAS* 102:4542-47 (2005), Herr et al., *Genomics* 85(3):392-400 (2005), and Bignell et al., *Genome Res.* 14:287-95 (2004). The collection of probes may also be used as a semi-random representation of the entire genome. The array and collection of SNP probes and indel probes may be used for analysis of copy number, methylation, genetic rearrangements and to assess other genomic features.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition. Methods as described herein allow high-density microarrays to include discrimination of indel alleles, including complex and multi-base indels, that were not possible on such large scale arrays, making for an expanded list of diseases that can be characterized with DNA array technology or other probe-based analysis.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions. A greater range of testing using gene arrays is possible by incorporating indel probes designed as described herein.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531-537 (2001) hereby incorporated by reference in its entirety for all purposes.) The arrays may be used for any application that uses genotype information, for examples, applications such as pharmacogenomics, translational medicine, paternity analysis, linkage, association, allele frequency determination, relatedness determination, forensics and genetic mapping.

Embodiment in a Programmed Information Appliance

Figure 2:
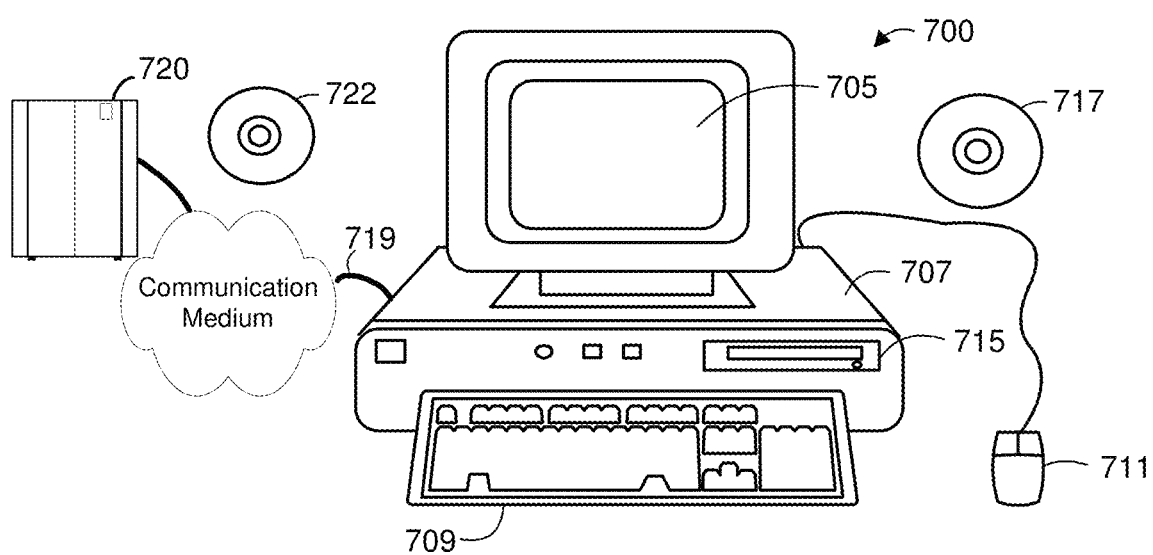
FIG. 2 is a block diagram showing a representative example logic device in which various aspects of the present invention may be embodied.

FIG. 2 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a user on a fixed media for physically loading into a user's computer or a fixed media containing logic instructions may reside on a remote server that a user accesses through a communication medium in order to download a program component.

FIG. 2 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

Other Embodiments

The invention has now been described with reference to specific embodiments. Other embodiments will be apparent to those of skill in the art. In particular, a user digital information appliance has generally been illustrated as a personal computer. However, the digital computing device is meant to be any information appliance for interacting with a remote data application, and could include such devices as a digitally enabled television, cell phone, personal digital assistant, laboratory or manufacturing equipment, etc. It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

The general structure and techniques, and more specific embodiments which can be used to effect different ways of carrying out the more general goals are described herein.

Although only a few embodiments have been disclosed in detail above, other embodiments are possible and the inventor (s) intend these to be encompassed within this specification. The specification describes specific examples to accomplish a more general goal that may be accomplished in another way. This disclosure is intended to be exemplary, and the claims are intended to cover any modification or alternative which might be predictable to a person having ordinary skill in the art. For example, While Affymetrix™ arrays are described in the embodiments, other embodiments may use other types of DNA identification techniques.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

The computers described herein may be any kind of computer, either general purpose, or some specific purpose computer such as a workstation. The computer may be an Intel (e.g., Pentium or Core 2 duo) or AMD based computer, running Windows XP or Linux, or may be a Macintosh computer. The computer may also be a handheld computer, such as a PDA, cellphone, or laptop. The programs may be written in C or Python, or Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attached Storage (NAS), or other removable medium, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

What is claimed:

1. A method of providing a genotyping array for genotyping a plurality of complex or multi-base indels within one or more sample genomes, the method comprising:

accessing a data set of one or more genome databases, said data set comprising information regarding genomic locations of the plurality of complex or multi-base indels (insertion/deletion) and sequences flanking at least one direction of the indels;

designing a plurality of indel probes to generate a plurality of designed indel probes for inclusion on a genotyping array by using one or more computer processors coupled to one or more memories configured to provide the one or more computer processors with instructions to, for each complex or multi-base indel of the plurality of complex or multi-base indels:

(a) access or generate a probe sequence that is complementary to a target sequence flanking the complex or multi-base indel;

(b) compare a deletion allele interrogation base to an insertion allele interrogation base in an indel identification sequence, the deletion allele interrogation base and the insertion allele interrogation base being referred to collectively as the interrogation bases, and, (c) in response to the interrogation bases being different and being in different detection channels, create and output a single indel probe adapted for using the interrogation bases to differentiate the deletion allele and the insertion allele; and (d) in response to the compared interrogation bases being a same interrogation base, incorporate the same interrogation base into the probe sequence and set new interrogation bases to be compared based on a next downstream base in a deletion allele sequence and a next downstream base in an insertion allele sequence and repeat (b)-(c) until either an interrogation distance threshold would be exceeded or the interrogation bases are different and are in different detection channels, and, when the interrogation bases are different and are in different detection channels, create and output a single indel probe adapted for using the interrogation bases to differentiate the deletion allele and the insertion allele;

synthesizing a plurality of indel probes of the genotyping array according to the plurality of designed indel probes; and providing, with the genotyping array, labelled nucleotide bases corresponding to the interrogation bases for adding to a corresponding probe of the plurality of synthesized probes after the corresponding probe is hybridized with a sample during a genotyping assay, interrogation bases corresponding to some of the plurality of synthesized indel probes having different interrogation distances than do interrogation bases corresponding to others of the plurality of synthesized indel probes, a complex or multi-base indel of the plurality of complex or multi-base indels being genotyped by detecting labels corresponding to the labelled nucleotide bases.

2. The method of claim 1 wherein the instructions comprise instructions to:

(e) in response to the compared interrogation bases being different and being in the same detection channel, determine allele-specific oligonucleotides (ASO) for creating-two different indel probes, one for the insertion allele and one for the deletion allele by moving one base downstream in an insertion allele sequence and one base downstream in a deletion allele sequence to incorporate the compared interrogation bases, respectively, into each indel probe;

(f) identify a new interrogation base for a first probe that measures a first of the alleles;

(g) move downstream one base in a sequence of a second of the alleles to incorporate a base one downstream of the compared interrogation bases into a second probe that measures a second of the alleles;

(h) identify a new interrogation base for the second probe and compare to the new interrogation base for the first probe;

(i) repeat (g) and (h) until the new interrogation bases are the same or an interrogation distance threshold is exceeded;

(j) when an interrogation distance threshold is first exceeded, switch the second probe to the first probe and repeat (f), (g), and (h) until an identical interrogation base is found or an interrogation distance threshold is exceeded; and (k) output the first and second probes as allele-specific oligonucleotides indel probes.

3. The method of claim 1 wherein the instructions comprise instructions to:

in response to the compared bases being different and being in the same detection channel, determine allele-specific oligonucleotides (ASO), creating two ASO probes comprising an insertion probe and a deletion probe for two different alleles by:

sliding one base downstream and incorporate the previous compared base into each ASO probe; and for both the insertion and deletion probes, using a next base as a new interrogation base;

wherein determining final allele-specific probes requires the addition of only a single additional base into the deletion probe and the insertion probe.

4. A method for genotyping a plurality of complex or multi-base indels within one or more sample genomes comprising:

for each synthesized indel probe of a plurality of synthesized indel probes, adding one or more nucleotides or oligonucleotides including a label to the synthesized indel probe after hybridization with a sample, the one or more nucleotides or oligonucleotides being added corresponding to an interrogation base; and genotyping a complex or multi-base indel of the plurality of complex or multi-base indels by detecting a respective label corresponding to a respective one or more nucleotides or oligonucleotides added to a respective synthesized indel probe of the plurality of synthesized indel probes;

wherein the plurality of synthesized probes have been designed by steps comprising:

accessing a data set of one or more genome databases, said data set comprising information regarding genomic locations of the one or more complex or multi-base indels (insertion/deletion) and sequences flanking at least one direction of the indels;

for each of the plurality of indel probes to be designed, designing the indel probe by:

(a) generating a probe sequence that is complementary to a target sequence flanking the complex or multi-base indel, and comparing interrogation bases in an indel identification sequence for a deletion allele probe and for an insertion allele probe; and (b) if the compared interrogation bases are different and are in different detection channels, creating and outputting a single indel probe using the interrogation bases to differentiate the indel alleles and END;

(c) if the compared interrogation bases are different and in the same detection channel, EXIT (a)-(c);

(d) if the compared interrogation bases are the same, repeating beginning at step (a), but setting the interrogation base one base downstream of the previously compared interrogation base as a current compared interrogation base and increasing an interrogation distance counter by one until a base after the indel identification sequence differs from a prior base of the indel and when the interrogation bases, after the downstream setting, are different and are in different detection channels, creating and outputting a single indel probe using the interrogation bases to differentiate the deletion allele and the insertion allele; and (e) repeating steps a-c until (b OR c) is TRUE or until an interrogation distance threshold is exceeded;

wherein designing results in a plurality of designed indel probes such that interrogation bases corresponding to some of the plurality of designed indel probes have different interrogation distances than do interrogation bases corresponding to others of the plurality of designed indel probes.

5. The method of claim 4 wherein indel probes are compatible with a system and analysis software using SNP probes to identify single nucleotide polymorphisms (SNPs) by detecting the identity of an interrogation base added to the SNP probes.

6. The method of claim 4 wherein creating and outputting a single SNP probe further comprises:

storing data representing the single SNP probe on a tangible media either immediately or after design of a plurality of SNP probes.

7. The method of claim 4 wherein creating and outputting a single SNP probe further comprises:

creating an oligonucleotide probe and configuring the oligonucleotide probe with other probes for use in an oligonucleotide array.

8. The method of claim 4 further comprising:

if the compared bases are different and in the same detection channel, EXIT (a)-(c) and determine allele-specific oligonucleotides (ASO), creating two different indel probes for the insertion allele and the deletion allele by:

sliding one base downstream and incorporating the previous interrogation base into each ASO probe; and identifying a new interrogation base for the probe that measures the deletion;

sliding downstream one base the probe that measures the insertion until an identical interrogation base is found;

determining final allele-specific indel probes.

9. The method of claim 8 further comprising:

if no nearby identical interrogation base can be found, sliding the deletion or insertion probe one base downstream and retrying a number of times until an interrogation distance threshold is exceeded.

10. The method of claim 4 further comprising:

if the compared bases are different and in the same detection channel, EXIT (a)-(c) and determine allele-specific oligonucleotides (ASO), creating two different indel probes for the insertion allele and the deletion allele by:

sliding one base downstream and incorporating the previous interrogation base into each ASO probe; and identifying a new interrogation base for the probe that measures the insertion;

sliding downstream one base the probe that measures the deletion until an interrogation base in the same detection channel is found;

determining final allele-specific indel probes.

11. The method of claim 10 further comprising:

if no nearby interrogation base in the same channel can be found, sliding deletion (or insertion) probe one downstream and retrying a number of times until an interrogation distance threshold is exceeded.

12. The method of claim 11 further comprising:

if the interrogation distance threshold is exceeded or if either the insertion or deletion probe has an interrogation distance greater than a threshold, repeating using the other probe and comparing resulting ASO indel probes.

13. The method of claim 4 further comprising:

if the compared bases are different and in the same detection channel, EXIT (a)-(c) and determine allele-specific oligonucleotides (ASO), creating two probes for two different alleles by:

sliding one base downstream and incorporating the previous compared base into each ASO probe; and for both the insertion and deletion probes, using the next base as the new interrogation base;

determining final allele-specific probes wherein effectively requiring only the addition of a single additional base into the ASO probe for both the deletion and the insertion probe.

14. The method of claim 4 further comprising:

creating indel probes from both left and right sides.

15. The method of claim 4 wherein indel probes are designed so that each indel is represented by a collection of indel probes.

\* \* \* \* \*